United States Patent [19]

Card et al.

[11] Patent Number: 5,234,814
[45] Date of Patent: Aug. 10, 1993

[54] DIAGNOSTIC ASSAY FOR ALZHEIMER'S DISEASE

[75] Inventors: John P. Card, Wilmington; Leonard G. Davis, Newark; Robert G. Siman, Wilmington, all of Del.

[73] Assignee: Du Pont Merck Pharmaceutical Company, Wilmington, Del.

[21] Appl. No.: 359,822

[22] Filed: Jun. 1, 1989

[51] Int. Cl.$^5$ ............... G01N 33/543; G01N 33/561; C07K 13/00; C07K 3/26
[52] U.S. Cl. .................... 435/7.21; 435/7.92; 436/516; 530/350; 530/395
[58] Field of Search ............ 435/6, 5, 7.2, 7.92, 435/7.21; 436/516; 530/350, 395

[56] References Cited

U.S. PATENT DOCUMENTS 4,666,829  5/1987  Glenner et al. .

FOREIGN PATENT DOCUMENTS 274826   7/1988  European Pat. Off. .
285159  10/1988  European Pat. Off. .
109443  11/1987  Japan .
WO89/01343  2/1989  PCT Int'l Appl. .

OTHER PUBLICATIONS

Weidemann et al., "Identification, Biogenesis, and Localization of Precursors of Alzheimor's Disease", Cell 57, 115-126 (1989).
Palmert et al., Biochem. Biophys. Res. Comm 165: 182-188 (1989).
Palmert et al., Proc. Natl. Acad. Sci. 86:6338-6342 (1989).
Estus et al., Science 255:726-728 (1992).
Golde et al., Science 255:728-730 (1992).
Abraham et al., Bio/Technology 7:147-153.
McDonald et al., Alzheimer Disease & Associated Disorders, p. 186, vol. 2, No. 3 (1988).
Selkoe et al., Proc. Natl. Acad. Sci. USA, pp. 7341-7345, vol. 85 (Oct. 1988).
Simpson et al., FEBS, pp. 196-198, vol. 237, No. 1,2 (Sep. 1988).
Palmert et al., Biochem. Biophys. Res. Commun., pp. 432-437, vol. 156, No. 1 (Oct. 14, 1988).
Zimmerman et al., EMBO, pp. 367-372, vol. 7, No. 2 (1988).
Shivers et al., EMBO, pp. 1365-1370, vol. 7, No. 5 (1988).
Dyrks et al., EMBO, pp. 949-957, vol. 7, No. 4 (1988).
Neve et al., Abst. Natl. Inst. on Aging Mtg. on Mol. & Cell. Mech. of Neural Plas. in Aging & Alzheimer's Disease, p. 30 (May 1989).
Selkoe, Abst. Natl. Inst. on Aging Mtg. on Mol. & Cell. Mech. of Neural Plas. in Aging & Alzheimer's Disease, p. 31 (May 1989).
Breyreuther et al., Abst. Inst. on Aging Mtg. on Mol. & Cell. Mech. of Neural Plas. in Aging & Alzheimer's Disease, p. 32 (May 1989).
Pardridge et al., Biochem. Biophys. Res. Commun., pp. 241-248, vol. 145, No. 1 (May 29, 1987).
Allsop et al., Neuroscience Letters, pp. 252-256, vol. 68 (1986).
Allsop et al., PNAS (USA), pp. 2790-2794 (Apr. 1988).
Bendheim et al., Nature, pp. 418-421, vol. 310 (Aug. 2, 1984).
Hollander et al., Neurobiology of Aging, pp. 367-387, vol. 7, (1986).
Ishii et al., Neuropathology & Applied Neurobiology, pp. 441-445, vol. 12 (1986).
MacDonald et al., J. Clin. Pathol., pp. 1199-1203, vol. 39 (1986).

(List continued on next page.)

*Primary Examiner*—Christine M. Nucker
*Assistant Examiner*—M. P. Woodward
*Attorney, Agent, or Firm*—Blair Q. Ferguson; Lynne M. Christenbury

[57] ABSTRACT

A method to assist in the diagnosis of Alzheimer's disease comprising detecting, in bodily fluids, two APP-related proteins, in soluble form, said proteins have an apparent molecular size of about 130 kDa and about 35 kDa, and each of said proteins shares at least one epitope with the C-terminus of APP corresponding substantially to amino acids 676-695 of APP as shown in FIG. 1.

4 Claims, 5 Drawing Sheets

OTHER PUBLICATIONS

Masters et al., EMBO J, pp. 2757-2763, vol. 4 (1985).
Powers et al., J. Neuropathology & Experimental Neurology, pp. 592-612, vol. 40, No. 6 (Nov. 1981).
Seikoe et al., Science, pp. 873-877 vol. 235 (1987).
Wolozin et al., Science, pp. 648-650, vol. 232 (May 2, 1986).
Wong et al., PNAS (USA), pp. 8729-8732, vol. 82 (Dec. 1985).
Carrell, Nature, pp. 478-479, vol. 331 (Feb. 11, 1988).
Coria et al., Lab. Invest., pp. 454-458, vol. 58, No. 4 (1988).
Glenner et al., Biochem. Biophys. Res. Commun., pp. 885-890, vol. 120, No. 3 (1984).
Glenner, New England J. Med., pp. 1283-1292, vol. 302 (1980).
Glenner, New England J. Med., pp. 1333-1343, (1980).
Glenner et al., Biochem. Biophys. Res. Commun., pp. 1287-1289, vol. 41, No. 5 (1970).
Glenner et al., Biochem. Biophys. Res. Commun., pp. 1131-1135, vol. 122, No. 3 (1984).
Glenner et al., Cell., pp. 307-308, vol. 52 (Feb. 12, 1988).
Kidd et al., The Lancet, p. 278, vol. 1 (Feb. 2, 1985).
Kitaguchi et al., Nature, pp. 530-532, vol. 331 (Feb. 11, 1988).
Linke et al., PNAS (USA), pp. 1473-1476, vol. 72, No. 4 (Apr. 1975).
Marx, Science, pp. 1664-1666, vol. 243 (Mar. 31, 1989).
Nikkaido et al., Arch. Neurol., pp. 198-211, vol. 25 (Sep. 1975).
Ponte et al., Nature, pp. 825-827, vol. 331 (Feb. 11, 1988).
Robakis et al., PNAS (USA), pp. 4190-4194, vol. 84 (Jun. 1987).
Sipe et al., J. Immunol., pp. 1151-1156, vol. 116, No. 4 (Apr. 1976).
Tanzi et al., Nature, pp. 528-530, vol. 331 (Feb. 11, 1988).
Anderton et al., Nature, pp. 84-86, vol. 298 (Jul. 1, 1982).
Anderton et al. TINS, pp. 337-338 (Aug. 1986).
Duyckaerts et al., Acta Neuropathol. (Berl), pp. 167-170, vol. 73 (1987).
Emory et al., Neurology, pp. 768-772, vol. 37 (1987).
Grandke-Iqbal et al., Acta. Neuropathol., pp. 279-283, vol. 68 (1985).
Ihara et al., Nature, pp. 727-730, vol. 304 (Aug. 25, 1983).
Iqbal et al., Brain Research, pp. 321-332, vol. 142 (1978).
Kirschner et al., PNAS (USA), pp. 695-697, vol. 84 (Oct. 1987).
Kosik et al., PNAS, pp. 7941-7945, vol. 81 (1984).
Majocha et al., J. Geriatric Psychiatry Neurology, pp. 65-70, vol. 1 (1988).
Marotha et al., Neuroscience, p. 1151, vol. 13 (1988).
Science, pp. 1260 and 1324, vol. 230 (Dec. 13, 1986).
Mattiace et al., Neuroscience, p. 1151, vol. 13 (1988).
Rasool et al., Brain Res., pp. 194-198, vol. 322 (1984).
Rasool et al., Brain Res. pp. 249-260, vol. 310 (1984).
Selkoe et al., Neuroscience, vol. 13 (1988), Abstract 1150.
Wood et al., J. Neurochem., pp. 149-154, vol. 44 (1985).
Yen et al., Am. J. Pathol., pp. 373-381, vol. 113 (1983).
Richardson et al., Eur. J. Nucl. Med., pp. 313-320, vol. 12 (1986).
O'Grady et al., Am. J. Physiologic Imaging, pp. 44-53, vol. 1 (1986).
Haber, Am. Rev. Med., pp. 249-261, vol. 37 (1986).
Andreasen, Science, pp. 1381-1388, vol. 239 (Mar. 18, 1988).
Ishii et al., Acta Neuropathol (Berl), pp. 296-300, vol. 63 (1984).
Masters et al., PNAS (USA), pp. 4245-4249, vol. 82 (1985).
McKhann et al., Neurology, pp. 939-944, vol. 34 (Jul. 1984).
McGeer, Br. Med. Ball., pp. 24-28, vol. 42, No. 1 (1986).
Nagel et al., (Current Concepts in Diagnostic Nuclear Medicine, pp. 4-8 (Fall 1987).
Roth et al., Nature, pp. 109-110, vol. 209, No. 5018 (Jan. 1, 1966).
Sochurek, Natl. Geog. Soc., pp. 2-41 (Jan. 1987).

FIG. 1A

```
         ATGCTGCCCGGTTTGGCACTGCTCCTGCTGGCCGCCTGGACGGCTCGGGCGCTGGAGGTA
    147  ---+----------+----------+----------+----------+----------+------ 206
         TACGACGGGCCAAACCGTGACGAGGACGACCGGCGGACCTGCCGAGCCCGCGACCTCCAT c     M  L  P  G  L  A  L  L  L  L  A  A  W  T  A  R  A  L  E  V    -

CCCACTGATGGTAATGCTGGCCTGCTGGCTGAACCCCAGATTGCCATGTTCTGTGGCAGA
    207  ---+----------+----------+----------+----------+----------+------ 266
         GGGTGACTACCATTACGACCGGACGACCGACTTGGGGTCTAACGGTACAAGACACCGTCT c     P  T  D  G  N  A  G  L  L  A  E  P  Q  I  A  M  F  C  G  R    -

CTGAACATGCACATGAATGTCCAGAATGGGAAGTGGGATTCAGATCCATCAGGGACCAAA
    267  ---+----------+----------+----------+----------+----------+------ 326
         GACTTGTACGTGTACTTACAGGTCTTACCCTTCACCCTAAGTCTAGGTAGTCCCTGGTTT c     L  N  M  H  M  N  V  Q  N  G  K  W  D  S  D  P  S  G  T  K    -

ACCTGCATTGATACCAAGGAAGGCATCCTGCAGTATTGCCAAGAAGTCTACCCTGAACTG
    327  ---+----------+----------+----------+----------+----------+------ 386
         TGGACGTAACTATGGTTCCTTCCGTAGGACGTCATAACGGTTCTTCAGATGGGACTTGAC c     T  C  I  D  T  K  E  G  I  L  Q  Y  C  Q  E  V  Y  P  E  L    -

CAGATCACCAATGTGGTAGAAGCCAACCAACCAGTGACCATCCAGAACTGGTGCAAGCGG
    387  ---+----------+----------+----------+----------+----------+------ 446
         GTCTAGTGGTTACACCATCTTCGGTTGGTTGGTCACTGGTAGGTCTTGACCACGTTCGCC c     Q  I  T  N  V  V  E  A  N  Q  P  V  T  I  Q  N  W  C  K  R    -

GGCCGCAAGCAGTGCAAGACCCATCCCCACTTTGTGATTCCCTACCGCTGCTTAGTTGGT
    447  ---+----------+----------+----------+----------+----------+------ 506
         CCGGCGTTCGTCACGTTCTGGGTAGGGGTGAAACACTAAGGGATGGCGACGAATCAACCA c     G  R  K  Q  C  K  T  H  P  H  F  V  I  P  Y  R  C  L  V  G    -
```

FIG. 1B

```
     GAGTTTGTAAGTGATGCCCTTCTCGTTCCTGACAAGTGCAAATTCTTACACCAGGAGAGG
507  ---+---------+---------+---------+---------+---------+------  566
     CTCAAACATTCACTACGGGAAGAGCAAGGACTGTTCACGTTTAAGAATGTGGTCCTCTCC c      E  F  V  S  D  A  L  L  V  P  D  K  C  K  F  L  H  Q  E  R  -

ATGGATGTTTGCGAAACTCATCTTCACTGGCACACCGTCGCCAAAGAGACATGCAGTGAG
567  ---+---------+---------+---------+---------+---------+------  626
     TACCTACAAACGCTTTGAGTAGAAGTGACCGTGTGGCAGCGGTTTCTCTGTACGTCACTC c      M  D  V  C  E  T  H  L  H  W  H  T  V  A  K  E  T  C  S  E  -

AAGAGTACCAACTTGCATGACTACGGCATGTTGCTGCCCTGCGGAATTGACAAGTTCCGA
627  ---+---------+---------+---------+---------+---------+------  686
     TTCTCATGGTTGAACGTACTGATGCCGTACAACGACGGGACGCCTTAACTGTTCAAGGCT c      K  S  T  N  L  H  D  Y  G  M  L  L  P  C  G  I  D  K  F  R  -

GGGGTAGAGTTTGTGTGTTGCCCACTGGCTGAAGAAAGTGACAATGTGGATTCTGCTGAT
687  ---+---------+---------+---------+---------+---------+------  746
     CCCCATCTCAAACACACAACGGGTGACCGACTTCTTTCACTGTTACACCTAAGACGACTA c      G  V  E  F  V  C  C  P  L  A  E  E  S  D  N  V  D  S  A  D  -

GCGGAGGAGGATGACTCGGATGTCTGGTGGGGCGGAGCAGACACAGACTATGCAGATGGG
747  ---+---------+---------+---------+---------+---------+------  806
     CGCCTCCTCCTACTGAGCCTACAGACCACCCCGCCTCGTCTGTGTCTGATACGTCTACCC c      A  E  E  D  D  S  D  V  W  W  G  G  A  D  T  D  Y  A  D  G  -

AGTGAAGACAAAGTAGTAGAAGTAGCAGAGGAGGAAGAAGTGGCTGAGGTGGAAGAAGAA
807  ---+---------+---------+---------+---------+---------+------  866
     TCACTTCTGTTTCATCATCTTCATCGTCTCCTCCTTCTTCACCGACTCCACCTTCTTCTT c      S  E  D  K  V  V  E  V  A  E  E  E  E  V  A  E  V  E  E  E  -

GAAGCCGATGATGACGAGGACGATGAGGATGGTGATGAGGTAGAGGAAGAGGCTGAGGAA
867  ---+---------+---------+---------+---------+---------+------  926
     CTTCGGCTACTACTGCTCCTGCTACTCCTACCACTACTCCATCTCCTTCTCCGACTCCTT c      E  A  D  D  D  E  D  D  E  D  G  D  E  V  E  E  E  A  E  E  -

CCCTACGAAGAAGCCACAGAGAGAACCACCAGCATTGCCACCACCACCACCACCACCACA
927  ---+---------+---------+---------+---------+---------+------  986
     GGGATGCTTCTTCGGTGTCTCTCTTGGTGGTCGTAACGGTGGTGGTGGTGGTGGTGGTGT c      P  Y  E  E  A  T  E  R  T  T  S  I  A  T  T  T  T  T  T  T  -
```

FIG. 1C

```
     GAGTCTGTGGAAGAGGTGGTTCGAG*TTCCTACAACAGCAGCCAGTACCCCTGATGCCGTT
987  ---+----------+----------+----------+----------+----------+------ 1046
     CTCAGACACCTTCTCCACCAAGCTCAAGGATGTTGTCGTCGGTCATGGGGACTACGGCAA c      E  S  V  E  E  V  V  R  V  P  T  T  A  A  S  T  P  D  A  V   -

GACAAGTATCTCGAGACACCTGGGGATGAGAATGAACATGCCCATTTCCAGAAAGCCAAA
1047  ---+----------+----------+----------+----------+----------+------ 1106
      TGTTCATAGAGCTCTGTGGACCCCTACTCTTACTTGTACGGGTAAAGGTCTTTCGGTTT c      D  K  Y  L  E  T  P  G  D  E  N  E  H  A  H  F  Q  K  A  K   -

GAGAGGCTTGAGGCCAAGCACCGAGAGAGAATGTCCCAGGTCATGAGAGAATGGGAAGAG
1107  ---+----------+----------+----------+----------+----------+------ 1166
      CTCTCCGAACTCCGGTTCGTGGCTCTCTCTTACAGGGTCCAGTACTCTCTTACCCTTCTC c      E  R  L  E  A  K  H  R  E  R  M  S  Q  V  M  R  E  W  E  E   -

GCAGAACGTCAAGCAAAGAACTTGCCTAAAGCTGATAAGAAGGCAGTTATCCAGCATTTC
1167  ---+----------+----------+----------+----------+----------+------ 1226
      CGTCTTGCAGTTCGTTTCTTGAACGGATTTCGACTATTCTTCCGTCAATAGGTCGTAAAG c      A  E  R  Q  A  K  N  L  P  K  A  D  K  K  A  V  I  Q  H  F   -

CAGGAGAAAGTGGAATCTTTGGAACAGGAAGCAGCCAACGAGAGACAGCAGCTGGTGGAG
1227  ---+----------+----------+----------+----------+----------+------ 1286
      GTCCTCTTTCACCTTAGAAACCTTGTCCTTCGTCGGTTGCTCTCTGTCGTCGACCACCTC c      Q  E  K  V  E  S  L  E  Q  E  A  A  N  E  R  Q  Q  L  V  E   -

ACACACATGGCCAGAGTGGAAGCCATGCTCAATGACCGCCGCCGCCTGGCCCTGGAGAAC
1287  ---+----------+----------+----------+----------+----------+------ 1346
      TGTGTGTACCGGTCTCACCTTCGGTACGAGTTACTGGCGGCGGCGGACCGGGACCTCTTG c      T  H  M  A  R  V  E  A  M  L  N  D  R  R  R  L  A  L  E  N   -

TACATCACCGCTCTGCAGGCTGTTCCTCCTCGGCCTCGTCACGTGTTCAATATGCTAAAG
1347  ---+----------+----------+----------+----------+----------+------ 1406
      ATGTAGTGGCGAGACGTCCGACAAGGAGGAGCCGGAGCAGTGCACAAGTTATACGATTTC c      Y  I  T  A  L  Q  A  V  P  P  R  P  R  H  V  F  N  M  L  K   -

AAGTATGTCCGCGCAGAACAGAAGGACAGACAGCACACCCTAAAGCATTTCGAGCATGTG
1407  ---+----------+----------+----------+----------+----------+------ 1466
      TTCATACAGGCGCGTCTTGTCTTCCTGTCTGTCGTGTGGGATTTCGTAAAGCTCGTACAC c      K  Y  V  R  A  E  Q  K  D  R  Q  H  T  L  K  H  F  E  H  V   -
```

*Different exon utilization results in the insertion of additional amino acid sequences here leading to at least two alternate APP forms; other alternate forms of the APP gene expression may also exist.

FIG. 1D

```
        CGCATGGTGGATCCCAAGAAAGCCGCTCAGATCCGGTCCCAGGTTATGACACACCTCCGT
1467    ---+---------+---------+---------+---------+---------+------ 1526
        GCGTACCACCTAGGGTTCTTTCGGCGAGTCTAGGCCAGGGTCCAATACTGTGTGGAGGCA c    R  M  V  D  P  K  K  A  A  Q  I  R  S  Q  V  M  T  H  L  R   -

GTGATTTATGAGCGCATGAATCAGTCTCTCTCCCTGCTCTACAACGTGCCTGCAGTGGCC
1527    ---+---------+---------+---------+---------+---------+------ 1586
        CACTAAATACTCGCGTACTTAGTCAGAGAGAGGGACGAGATGTTGCACGGACGTCACCGG c    V  I  Y  E  R  M  N  Q  S  L  S  L  L  Y  N  V  P  A  V  A   -

GAGGAGATTCAGGATGAAGTTGATGAGCTGCTTCAGAAAGAGCAAAACTATTCAGATGAC
1587    ---+---------+---------+---------+---------+---------+------ 1646
        CTCCTCTAAGTCCTACTTCAACTACTCGACGAAGTCTTTCTCGTTTTGATAAGTCTACTG c    E  E  I  Q  D  E  V  D  E  L  L  Q  K  E  Q  N  Y  S  D  D   -

GTCTTGGCCAACATGATTAGTGAACCAAGGATCAGTTACGGAAACGATGCTCTCATGCCA
1647    ---+---------+---------+---------+---------+---------+------ 1706
        CAGAACCGGTTGTACTAATCACTTGGTTCCTAGTCAATGCCTTTGCTACGAGAGTACGGT c    V  L  A  N  M  I  S  E  P  R  I  S  Y  G  N  D  A  L  M  P   -

TCTTTGACCGAAACGAAAACCACCGTGGAGCTCCTTCCCGTGATTGGAGAGTTCAGCCTG
1707    ---+---------+---------+---------+---------+---------+------ 1766
        AGAAACTGGCTTTGCTTTTGGTGGCACCTCGAGGAAGGGCACTAACCTCTCAAGTCGGAC c    S  L  T  E  T  K  T  T  V  E  L  L  P  V  I  G  E  F  S  L   -

GACGATCTCCAGCCGTGGCATTCTTTTGGGGCTGACTCTGTGCCAGCCAACACAGAAAAC
1767    ---+---------+---------+---------+---------+---------+------ 1826
        CTGCTAGAGGTCGGCACCGTAAGAAAACCCCGACTGAGACACGGTCGGTTGTGTCTTTTG c    D  D  L  Q  P  W  H  S  F  G  A  D  S  V  P  A  N  T  E  N   -

GAAGTTGAGCCTGTTGATGCCCGCCCTGCTGCCGACCGAGGACTGACCACTCGACCAGGT
1827    ---+---------+---------+---------+---------+---------+------ 1886
        CTTCAACTCGGACAACTACGGGCGGGACGACGGCTGGCTCCTGACTGGTGAGCTGGTCCA c    E  V  E  P  V  D  A  R  P  A  A  D  R  G  L  T  T  R  P  G   -

TCTGGGTTGACAAATATCAAGACGGAGGAGATCTCTGAAGTGAAGATGGATGCAGAATTC
1887    ---+---------+---------+---------+---------+---------+------ 1946
        AGACCCAACTGTTTATAGTTCTGCCTCCTCTAGAGACTTCACTTCTACCTACGTCTTAAG c    S  G  L  T  N  I  K  T  E  E  I  S  E  V  K  M  D  A  E  F   -
```

FIG. 1E

```
         CGACATGACTCAGGATATGAAGTTCATCATCAAAAATTGGTGTTCTTTGCAGAAGATGTG
1947     ---+---------+---------+---------+---------+---------+------ 2006
         GCTGTACTGAGTCCTATACTTCAAGTAGTAGTTTTTAACCACAAGAAACGTCTTCTACAC c          R  H  D  S  G  Y  E  V  H  H  Q  K  L  V  F  F  A  E  D  V   -

GGTTCAAACAAAGGTGCAATCATTGGACTCATGGTGGGCGGTGTTGTCATAGCGACAGTG
2007     ---+---------+---------+---------+---------+---------+------ 2066
         CCAAGTTTGTTTCCACGTTAGTAACCTGAGTACCACCCGCCACAACAGTATCGCTGTCAC c          G  S  N  K  G  A  I  I  G  L  M  V  G  G  V  V  I  A  T  V   -

ATCGTCATCACCTTGGTGATGCTGAAGAAGAAACAGTACACATCCATTCATCATGGTGTG
2067     ---+---------+---------+---------+---------+---------+------ 2126
         TAGCAGTAGTGGAACCACTACGACTTCTTCTTTGTCATGTGTAGGTAAGTAGTACCACAC c          I  V  I  T  L  V  M  L  K  K  K  Q  Y  T  S  I  H  H  G  V   -

GTGGAGGTTGACGCCGCTGTCACCCCAGAGGAGCGCCACCTGTCCAAGATGCAGCAGAAC
2127     ---+---------+---------+---------+---------+---------+------ 2186
         CACCTCCAACTGCGGCGACAGTGGGGTCTCCTCGCGGTGGACAGGTTCTACGTCGTCTTG c          V  E  V  D  A  A  V  T  P  E  E  R  H  L  S  K̲  M̲  Q̲  Q̲  N̲   -

GGCTACGAAAATCCAACCTACAAGTTCTTTGAGCAGATGCAGAACTAG
2187     ---+---------+---------+---------+---------+---- 2234
         CCGATGCTTTTAGGTTGGATGTTCAAGAAACTCGTCTACGTCTTGATC c          G̲  Y̲  E̲  N̲  P̲  T̲  Y̲  K̲  F̲  F̲  E̲  Q̲  M̲  Q̲  N̲  *   -
```

DIAGNOSTIC ASSAY FOR ALZHEIMER'S DISEASE

FIELD OF THE INVENTION

This invention relates to an in vitro diagnostic assay to assist in the diagnosis of Alzheimer's Disease and, more particularly, to an assay for detecting, in bodily fluids, unique soluble amyloid precursor protein-related proteins, fragments thereof, which share at least one epitope with the C-terminus of APP.

BACKGROUND OF THE INVENTION

Alzheimer's Disease is a form of dementia marked by progressive intellectual deterioration without focal, motor or sensory signs. It is an insidious, progressive, debilitating disease of unknown etiology afflicting almost two million Americans, most of them elderly.

Definitive diagnosis of the disease is often difficult since many other disorders and neurological deficits are also accompanied by cognitive loss, and histological examination of brain biopsies is an unacceptable procedure in the majority of cases. Thus, only a very small percentage of the total population of Alzheimer's patients is diagnosed early, and those individuals successfully identified are often well advanced in the disease process. Moreover, multiple psychological and biological tests need to be performed to eliminate other non-Alzheimer's related causes of dementia (NIH Publication No. 84-2251, 1984). Consequently, appropriate treatments are difficult to plan. Determining whether one of the causes of dementia is Alzheimer's requires a tool which unequivocally detects Alzheimer's Disease or, at least, eliminates most of the non-Alzheimer's related causes of dementia.

Although the etiology of the disease is unknown, researchers have identified three histopathological structures which are present in the brains of Alzheimer's patients: neurofibrillary tangles, neuritic (senile) plaques, and cerebrovasculature plaques. Neurofibrillary tangles (NT) are intracellular accumulations of fibrous material in the cell bodies of affected neurons, mainly in the hippocampus, amygdala and neocortex. Neuritic and cerebrovascular plaques are found in highest concentration in the hippocampus and neocortex and result from a pathological deposition of amyloid precursor protein(s) (APP) or fragments thereof in these regions. It should be noted that the term amyloid, as used in a neuropathological context, refers to the deposition of APP and its fragments into plaques. This differs from the usage of the term in the general, histopathological context. Specifically, when applied to neuropathological plaques, the term most commonly refers to the A4 amino acid fragment of APP. In standard histopathological uses the term anyloid refers to a refractive, insoluble, noncellular material.

Formation of plaques is now known to be one of the earliest events in the progression of the disease (Terry et al., *J. Neuropathol. Exp. Neurol.* 46:262-268 (1987); Wisniewski et al., *Banbury Report*, Davies and Finch, eds. (Cold Spring Harbor Laboratory, NY, pp. 1-26 (1988))). The clinical significance of plaque formation has been highlighted by quantitative studies showing a significant correlation between the numbers of neuritic plaques and neurofibrillary tangles and the clinical severity of dementia (Roth et al., *Nature*, pp. 109-110, Vol. 50 (1966) and Blessed et al., *Br. J. Psych.*, pp. 797-805, Vol. 114 (1968)), i.e., the most serious cognitive deficits are correlated with the largest number of plaques. Correlation of cognitive deficits with plaque deposition has led to a concerted effort in recent years to define the plaque constituents and the mechanism(s) of plaque generation.

It has been demonstrated that an insoluble material known as $\beta$-amyloid (Selkoe et al. *Science* 115:1243-1245 (1982)); (Glenner and Wong *Biochem. Biophys. Res. Commun.* 122:885-890 (1984); Wong et al. *Proc. Natl. Acad. Sci.* U.S.A. 82:8729-8732 (1985)), $\beta$-protein, or A4 (Masters et al. *EMBO J.* 4:2757 (1985)), which was isolated from the birefringent amyloid core of plaques, is the principle pathological component of Alzheimer's Disease.

In 1984, Glenner and Wong (*Biochem. Biophys. Res. Comm.* 122:1131-1135 (1984)) isolated and determined the amino acid sequence of a peptidergic component of the cerebrovascular amyloid plaques. Additional work with peptides isolated from neuritic plaques from Alzheimer's and Down's syndrome patients was done because older Down's syndrome patients also develop progressive dementia quite similar to the dementia associated with Alzheimer's disease (Ellis et al. *Neurology* 24:101-106 (1974), Wong et al., *Proc. Nat. Acad. Sci.*, U.S.A., pp. 8729-8732, Vol. 82 (1985)). These additionally isolated peptides were characterized and all were found to contain an amino acid sequence which was similar or identical to that originally isolated and reported by Glenner.

The amino acid sequence determined by Glenner and Wong has enabled researchers to use standard recombinant DNA procedures to isolate cDNA clones that encode the mRNA for the precursor protein of this $\beta$-amyloid peptide (Kang et al. *Nature* 733 (1987); Tanzi et al. *Science* 235:877 (1987)); Robakis et al. *Proc. Natl. Acad. Sci. U.S.A.* 84:4190 (1987)). Additional research has demonstrated that alternate forms of the precursor mRNA and protein exist (Kitaguchi et al. *Nature*, pp. 530-532, Vol. 331 (1988); Tanzi et al. *Nature* 331:528-530 (1988); Ponte et al. *Nature*, pp. 525-527, Vol. 331 (1988)). Based on these cDNA sequences, the amino acid sequences of the entire protein molecule(s) can be predicted from the open reading frame/coding region of the mRNA. FIG. 1 sets forth the predicted amino acid sequence for APP. It was speculated that the protein would be membrane-bound, possibly a receptor molecule (Kang et al. *Nature* 325:733 (1987)). Additional reports supported the conclusion that the amyloid precursor protein (APP) is a membrane localized protein (Zimmerman et al. *EMBO J.* 7:367-372 (1988); Allsop et al. *Proc. Natl. Acad. Sci.*, pp. 2790-2794, Vol. 85 (1988)). More recently, an N-terminal fragment has been reported in the soluble fraction from tissue extracts (Palmert et al. cited in Abraham and Potter *Bio/Technology* 7:147-153 (1989)).

It is also mentioned in *Bio/Technology* 7:147-153 that protein studies indicated APP is a membrane glycoprotein which can be detected in two forms using immunoblotting—a membrane-bound form which can be stained with antibodies to the N-terminal and C-terminal portions and a soluble form detected only with N-terminal antibodies. It is further suggested that the soluble form lacks the C-terminus, including the $\beta$-protein. It is also mentioned that pulse chase experiments showed that the soluble, extracellular form is derived from the membrane-bound form, probably by proteolytic cleavage. Results of protein studies are presented in Table 1 appearing on page 150 of *Bio/Technology* as discussed above.

McDonald et al., Alzheimer Disease and Associated Disorders, page 186, Vol. 2, No. 3, 1988, have reported the characterization and purification of a protein present in the cerebrospinal fluid and serum of individuals with Alzheimer's Disease using a monoclonal antibody which reacts immunohistochemically with amyloid deposits. Immunoreactive proteins of apparent molecular size of 100 and 95 kDa were detected using this monoclonal antibody.

Selkoe et al., *Proc. Natl. Acad. Scil. U.S.A.*, pp. 7341-7345, Vol. 85 (October 1988), disclose the detection of a group of ~ ~110 to 135 kDa membrane-bound proteins in human brain, nonneural tissues and cultured cells found to contain APP mRNAs. These proteins were detected by immunoblot using antibodies specific to C-terminal peptides of the predicted precursor protein comprising either the 20 C-terminal amino acids (numbers 676-695) or the 15 C-terminal amino acids (numbers 681-695). No 35 kDa protein appears to have been detected. Detection of a soluble form of precursor proteins, sharing at least one epitope with the C-terminus of APP, in cerebrospinal fluid or other bodily fluids was not reported.

European Patent Application Publication No. 285,159, published on Oct. 5, 1988, describes a human amyloid related protein monoclonal antibody. It is mentioned in column 9 at lines 13-24 that this antibody is potentially useful to diagnose Alzheimer's dementia. The amyloid-related protein recognized by this antibody has a molecular size of about 42-45 kilodaltons.

European Patent Application Publication No. 274,826, published on Jul. 20, 1988, describes the generation of antibodies against recombinant Alzheimer's amyloid protein or immunogenic peptides thereof for cerebral fluid or serum diagnosis of Alzheimer's Disease. There is no indication that one soluble form of APP-related proteins sharing at least one epitope with the C-terminus of APP could be detected in bodily fluids.

Pardridge et al., *Biochem. and Biophys. Res. Commun.*, pp. 241-248, Vol. 145, (May 29, 1987), describes the development of a radioimmunoassay to detect amyloid (A4) peptide or its precursor in human serum or cerebrospinal fluid. A high molecular weight immunoreactive substance was detected in human serum and CSF samples. It is stated on page 245 that the immunoreactive substance in serum or CSF is a high molecular weight protein that is highly homologous or, possibly, identical to the A4 peptide precursor, but was not the amyloid peptide, per se. A synthetic peptide corresponding to the first 28 amino acids of the 43 amino acid A4 peptide coupled to bovine thyroglobulin was used to generate the polyclonal antiserum used to detect this protein.

Japanese Patent Application 62 [1987]-267,297, which was published on Nov. 19, 1987, discloses a monoclonal antibody which reacts against senile plaques. It is mentioned on page 15 that it might be useful in early diagnosis of senile dementia Alzheimer's Type by detecting $\beta$-amyloid or its precursor protein possibly present in serum or cerebrospinal fluid.

BRIEF DESCRIPTION OF THE DRAWINGS

FIG. 1(A-E) depicts the approximately 695 amino acid sequence deduced for APP. Numbering is according to Kang group.

SUMMARY OF THE INVENTION

A method to assist in the diagnosis of Alzheimer's disease comprising detecting, in bodily fluids, two APP-related proteins, in soluble form, having an apparent molecular size of about 130 kDa and about 35 kDa wherein each protein shares at least one epitope with the C-terminus of APP corresponding substantially to amino acids 676-695 as shown in FIG. 1 (numbering according to Kang group) or a subsequence thereof.

DETAILED DESCRIPTION OF THE INVENTION

The term Alzheimer's amyloid precursor protein (APP) refers to the approximately 695 amino acid sequence and the alternate forms which have been deduced as the putative sequence for the Alzheimer's amyloid precursor. FIG. 1 depicts the putative amino acid sequence for the 695 APP form, numbering according to the Kang group.

The term APP-related proteins refers to APP, its alternate forms, cross-immunoreactive fragments thereof, and other proteins which cross-immunoreact with antisera directed against peptide sequences of the APP protein.

The term A4 peptide refers to the approximately 42-43 amino acid sequence identified by Masters et al. While the first twenty-eight amino acids (termed $\beta$-amyloid) was identified by Glenner et al., *Biochem. and Biophys. Res. Commun.*, pages 885-890, Vol. 120, No. 3 (1984) and U.S. Pat. No. 4,666,829 which issued on May 19, 1987.

The term "corresponding substantially" means functional equivalents with conservative substitutions, additions or deletions also fall within the scope of this invention.

Surprisingly and unexpectedly, unique soluble forms of APP-related proteins, having apparent molecular sizes of about 130 kDa and 35 kDa, respectively and also sharing at least one epitope with the C-terminus of APP corresponding substantially to amino acids 676-695 of APP as shown in FIG. 1, were detected in cerebrospinal fluid (CSF) of Alzheimer's samples according to the procedure described below.

An approximately 130 kDa protein (hereinafter "130 kDa protein") was detected in soluble form in the CSF of all the Alzheimer's samples which were analyzed (14 samples). In contrast, the 130 kDa protein was not detected in 5 normal control samples. The 130 kDa protein was detected in CSF of 5 of 12 degenerative disease states (Parkinson's, Pick's, or Creutzfeldt-Jakob's), and in 4 of 5 aged samples having an unclear neurological status (liver cirrhosis, heart failure, alcoholism/infarcts, pneumonia, or acute hypoxia). It is believed that the 130 kDa protein is an APP-related protein which shares at least one epitope with the C-terminus of APP corresponding substantially to amino acids 676-695 of APP as depicted in FIG. 1 or a subsequence thereof. Results are presented in Table 1.

An approximately 35 kDa protein (hereinafter "35 kDa protein") in soluble form was detected in the CSF in ten Alzheimer's samples (the other four samples could not be analyzed as they were not resolved on the earlier gels and none of the samples are left).

The 35 kDa protein was not detected in the 5 normal control samples. It was detected in 6 of 12 degenerative diseases (Parkinson's, Pick's or Creutzfeldt-Jakob's), and in one of the aged samples having unclear neurological status (liver cirrhosis, heart failure, alcoholism/infarcts, pneumonia, or acute hypoxia); the other four aged samples having unclear neurological status were not analyzable for the reasons described above.

The 35 kDa protein also appears to be an APP-related protein which shares at least one epitope with the C-terminus of APP corresponding substantially to amino acids 676–695 of APP as depicted in FIG. 1 or a subsequence thereof. Thus, it is believed that by detecting these unique soluble forms of APP-related proteins having apparent molecular sizes of about 130 kDa and about 35 kDa in bodily fluids and which share at least one epitope with the C-terminus of APP as described above, will reduce some of the testing for the non-Alzheimer's causes of dementia. Results are presented in Table 1 below.

It should be noted that some individuals who are diagnosed as having Parkinson's disease may also suffer from Alzheimer's Disease. However, the diagnosis is not modified to reflect that Alzheimer's Disease is also present (NIH Publication No. 84-2251 (1984)). Thus, some of the Parkinson's samples which tested positive for the APP-related 130 kDa and 35 kDa proteins, might also have Alzheimer's Disease.

Regarding the detection of the 130 kDa and 35 kDa proteins in CSF samples taken from individuals suffering from Creutzfeldt-Jakob's disease or Pick's disease, it is interesting to observe that individuals suffering from these diseases exhibit plaque-like deposits. In particular, Pick's disease is a rare form of presenile dementia with specific pathologic findings. Histologically, there is marked neuronal loss, particularly in the outer three layers of cortex of the frontal lobes and anterior temporal lobes. Clinically, this process is indistinguishable from Alzheimer's disease. Creutzfeldt-Jakob is a well defined clinical disease state which was formerly classified as presenile dementia of unknown etiology. It is unclear to what extent amyloid is associated with Creutzfeldt-Jakob disease.

These APP-related proteins were detected using an immunoblot. It was important that the samples were concentrated to a total protein concentration in the range from about 1.0 mg/ml to about 3.5 mg/ml using conventional techniques, such as ultrafiltration, freeze drying, evaporation, reverse osmosis, etc. The preferred concentration was about 2.5 mg/ml. Those skilled in the art will appreciate that the protein concentration desired can vary depending upon the sensitivity of the reporter system and affinity of the antibodies as well as the quality of the samples. Thus, the desired concentration can vary depending upon these factors.

In addition to cerebrospinal fluid, a variety of other bodily fluids such as blood, plasma, serum, urine and the like, can be used in the assay of this invention.

Proteins in the samples were separated by SDS-polyacrylamide gel electrophoresis on 5 to 15% linear gradient gels as described below.

APP specific antibodies were generated against various polypeptides corresponding to subsequences of the APP using conventional techniques as is described below. It is also within the scope of this invention to use monoclonal antibodies or immunoreactive fragments thereof to identify the presence of amyloid precursor protein, fragments thereof, and abnormalities in APP structure or physiological levels that might exist in the disease state when compared to results obtained from normal samples.

Monoclonal antibodies can be generated using the immunogens described below as well as other immunogens based on the APP sequence set forth in FIG. 1 and standard hybridoma technology such as that described in U.S. Pat. No. 4,196,265 and Kohler et al., *Nature*, pages 495–497 Vol. 256 Aug. 7, 1975).

For example, Balb/c×C57B16 mice can be immunized with the polypeptides coupled to a carrier protein such as keyhole limpet hemacyanin via the glutaraldehyde method of A. Kagan et al., *Methods of Hormone Radioimmunoassay*, pp 327–339 (2d Ed.) (1979). It is also possible to immunize mice with uncoupled polypeptides as was done and as described below.

Three days after an intraperitoneal boost the spleens of the appropriate immune mice are removed and fused with a non-secretor myeloma cell. Spleen cell suspensions are prepared in serumless DMEM-high glucose medium and mixed with myeloma cells at a ratio of 4:1. This cell mixture is centrifuged at 1200 g for 10 minutes at room temperature. After removal of the supernatant, the cells are resuspended by gently tapping the tube. The fusion procedure is initiated by adding 1.0 ml of 45% w/v polyethylene glycol 3350 (Baker) at 37° C. over a 30-second period.

The cells are occasionally mixed with a pipette tip for 90 seconds and 5 ml of serumless DMEM-high glucose medium is added over a 3-minute period. This is followed by the addition of 14 ml of DMEM-high glucose supplemented with 10% fetal calf serum, L-glutamine, hypoxanthine, aminopterin and thymidine (referred to as HAT medium). The HAT medium is added over a 1-minute period.

Appropriate volumes of HAT medium are added to cells and then the cells are centrifuged at 800× g for 7 minutes at room temperature. Supernatants are aspirated and the cell pellet is disrupted with 10 ml of HAT medium. Peritoneal cells from Balb/c×C57B1/6 are added and the final volume adjusted so that two hundred thousand spleen cells are dispensed to each well. Approximately 14 days later, tissue culture supernatants from wells containing hybridoma colonies are tested by ELISA for the desired reactivity with peptides conjugated to other carrier proteins.

It was found that the sensitivity of detection by immunoblot increased about three-fold by incubating the APP-specific-antibody-APP-related proteins complex with a detector system which comprised two detector reagents at two different dilutions after concentrating protein from the samples to a desired level. Following incubation with the rabbit anti-APP antibody, the next incubation should be with a dilution of the first detector reagent at a dilution determined empirically based on its titer and affinity for the initial antibody. Typically, the dilution of the first detector reagent is about one to about six-fold less than that of the second detector reagent. The second detector is used to amplify the signal due to its affinity for the first detection system. The increased sensitivity appears to be related to the presence of additional complexes that form first from a goat anti-rabbit antibody followed by incubation with a rabbit anti-goat antibody.

Those skilled in the art will appreciate that the detector system can include any reagent or combination of reagents suitable for detecting proteins in an immunoblot format. Typically, an anti-antibody coupled to a reporter is used as a detector reagent. Examples of reporters include enzymes, such as, horseradish peroxidase and alkaline phosphatase, radioisotopes, chemiluminescent, fluorogenic or electrochemical materials. Various coupling techniques are known to those skilled in the art.

The following examples illustrate the invention:

EXAMPLE 1

Production of APP-Specific Antibodies

Synthetic peptides, based on the amyloid precursor protein predicted amino acid sequence, were used as antigens to generate antibodies that could identify the entire APP. The peptides were synthesized by C. Brady (Du Pont) under the direction of J. Kauer using the RAMPS ™ method. These peptides corresponded substantially to amino acids numbered 599 to 618, 619 to 638, and 676 to 695 of the predicted amino acid sequence for APP (numbering was according to Kang group):

599 to 618:
GluPheArgHisAspSerGlyThrGluValHisHisGluLysLeuValPhePheAlaGlu 619 to 638:
AspValGlySerAsnLysGlyAlaIleIleGlyLeuMetValGlyGlyValValIleAla 676 to 695:
LysMetGlnGlnAsnGlyTyrGluAsnProThrTyrLysPhePheGluGlnMetGlnAsn

Three antisera, designated as numbers 382, 384 and 385, respectively, were generated. As detailed below, these antibodies proved useful in identifying the amyloid precursor.

The APP-specific antibodies (#382, 384, 385) were raised by repeated injection of each unconjugated peptide into separate female New Zealand albino rabbits. Initially, 0.5 mg peptide was injected at multiple subdermal sites in Freund's complete adjuvant. Subsequent booster injections of 0.2 mg peptide were performed at 3 to 4 week intervals using Freund's incomplete adjuvant. Rabbits were bled 7 to 14 days after the booster injections.

Serum titers were determined by using the following enzyme-linked immunosorbent assay (ELISA): peptides were bound to wells of polyvinyl microtiter plates (1 µg/well) which had been pre-treated with 0.1% glutaraldehyde to facilitate peptide adhesion. Serial dilutions of serum samples in bovine serum albumin (hereinafter "BSA") BSA-phosphate buffered saline were added to the wells which had been preblocked with BSA. The samples were incubated for one hour. Bound antibodies were detected by incubating the bound antigen-antibody complex with goat anti-rabbit IgG antibody conjugated to alkaline phosphatase which was then reacted with paranitrophenylphosphate substrate solution. Antisera yielding half-maximal signals in the ELISA at dilutions of 1:500 or higher were stored at −80° C.

EXAMPLE 2

Immunohistochemical Analysis Using APP-Specific Antibodies

Two of the antisera (#384 and #385) were subjected to rigorous immunohistochemical analysis in order to establish their specificity and determine the localization of the precursor protein in the rat central nervous system. The antisera were used in combination with the avidin-biotin modification (Hsu et al. *J. Histochem.* 29:577–580 (1981)) of the Sternberger (*In Immunocytochemistry*, Colan and McClusky, eds. (Wiley, N.Y.) pp. 104–169 (1979)) immunoperoxidase procedure, to localize the precursor protein at both the light and electron microscopic level. The details of these procedures have been published previously (Card et al. *Neuron* 1:835–846 (1988)). Standard procedures are described in Hsu et al. above and are also described below. Sections of buffered aldehyde-fixed tissue were incubated in various dilutions of primary antisera for a period of 24 to 48 hours at 4° C., followed by sequential exposure to a biotinylated secondary antiserum and the avidin-biotin-peroxidase solution. Diaminobenzidine and hydrogen peroxide were then utilized to visualize antigen localization. Tests of specificity included blocking of each antiserum with its native antigen (i.e., blocking of antiserum #385 with the antigen used to generate the antiserum #385) as well as cross blocking preabsorptions of each antiserum with other peptide fragments. Antisera were preincubated with 10 µM, 50 µM, and 100 µM concentrations of antigen for 90 minutes at room temperature prior to placing tissue sections in the antiserum. Blocking each antiserum with its native antigen eliminated all immunoreactivity, while cross blocking preabsorptions did not compromise immunohistochemical staining. Each test of specificity was run in parallel to immunohistochemical localization of the precursor protein with unblocked antisera to verify the success of the immunohistochemical procedure.

Immunohistochemical localizations with the #384 and #385 antisera revealed identical populations of cells throughout the rodent neuraxis. Extensive, but circumscribed, populations of immunoreactive neurons were present in all areas of the CNS with the largest concentration of cells occurring in the olfactory bulb, the cerebral cortex, the basal forebrain and the hippocampus. This localization of the precursor protein in hippocampus and cortex was consistent with studies in human brain which identified the amyloid precursor mRNA in the same areas using in situ hybridization. The cortex was also distinguished by a small, but distinct, population of immunoreactive astrocytes.

These studies were extended to human tissue in cortex and hippocampus with all three antisera. Antisera (including #382) were also used in immunocytochemical analysis of human brain from normal and Alzheimer's disease patients. Antiserum number 382 identified neuropathological plaques in both the cortex and hippocampus of Alzheimer's patients. Antiserum number 384 identifies both plaques and reactive astroglia in cortex and hippocampus of Alzheimer's brain. Antiserum number 385 did not prove useful for immunocytochemical localizations in human brain.

EXAMPLE 3

Immunoblot Analysis of Human Cerebrospinal Fluid Samples

Cerebrospinal fluid (CSF) samples from patients suffering from Alzheimer's disease (diagnosis confirmed post-mortem) or Parkinson's disease or controls with no history of neurological problems were obtained from the National Neurological Research Bank (Los Angeles, Calif.). Samples were concentrated by ultrafiltration over Amicon YM-30 membranes. Protein concentrations were determined by the method of Bradford (*Anal. Biochem.* 72:248,254 (1976)) and were equalized. Proteins in the CSF samples were separated by SDS-polyacrylamide gel electrophoresis on 5 to 15% linear gradient gels as previously described (Siman et al. *Proc. Natl. Acad. Sci. USA* 81:3572-3576 (1984)) and were transferred to nitrocellulose filters by the Western blot technique (Towbin et al. *Proc. Natl. Acad. Sci.* 76:4350:4354 (1979); Siman et al. *J. Neurosci.* 7:55-64 (1987)) and blocked for 60 min with 5% dry milk in Tris-buffered saline (TBS). Filters were then incubated for 2 hours at 23° C. with APP specific antibody #385 at 1:300 dilution in dry milk/TBS. After three 5 min washes with TBS+0.05% Tween-20 (TTBS), filters were incubated for 1 hour with goat anti-rabbit IgG-alkaline phosphatase (Bio-Rad) at 1:2000 dilution in dry milk/TBS. After 3 TTBS washes, filters were incubated a second time for another hour with rabbit anti-goat IgG antibody coupled to alkaline phosphatase (Cappel) at 1:500 dilution in dry milk/TBS. Filters were washed twice with TTBS, twice with TBS and were developed in the dark for 30 to 45 min with alkaline phosphatase substrate solution consisting of BCIP/NBT (kit obtained from Bio-Rad). Dried, stained blots were photographed with Polaroid type 55 film. Antibodies #382 and #384 were also evaluated in this procedure.

CSF samples from 14 Alzheimer's disease patients, 9 Parkinson's disease patients, and 5 controls, and 13 others were examined by the immunoblot method. Initially, 6 Alzheimer's samples and 5 controls were concentrated by ultrafiltration over Amican YM-30 membranes to a total protein concentration of 1 mg/mL; the remaining analysis was performed on samples concentrated to 2.5 mg/mL. The optimal concentration was determined empirically, i.e., it was desired to shorten the time it took for signal to appear.

All 14 of the 14 Alzheimer's samples were found to contain a polypeptide of apparent molecular size of about 130 kDa that reacted with antibody #385 prepared against the C-terminal portion of the β-amyloid precursor protein (APP) (amino acids 676–695). Other domains of APP can also be used to generate antibodies. Among the Parkinson's disease and other samples, 9 of 22 samples contained the 130 kDa polypeptide in detectable levels.

Results discussed above are presented in Table 1.

TABLE 1[a]

| SAMPLE NO. | AGE/SEX | DIAGNOSIS | 130 kD | 35 kD |
|---|---|---|---|---|
| 7783 | 80/M | Alzheimer's | + | |
| 7790 | 75/M | Alzheimer's | + | |
| 9203 | 86/M | Alzheimer's | + | |
| 9294 | 76/M | Alzheimer's | + | |
| 9403 | 74/F | Alzheimer's | + | + |
| 8637 | 74/F | Alzheimer's | + | + |
| 8278 | 64/F | Alzheimer's | + | + |
| 8119 | 68/F | Alzheimer's | + | + |
| 9314 | 72/F | Alzheimer's | + | + |
| 9277 | 69/M | Alzheimer's | + | + |
| 9262 | 64/M | Alzheimer's | + | + |
| 9368 | 70/F | Alzheimer's | + | + |
| 9373 | 67/F | Alzheimer's | + | + |
| 5116-A | 67/M | Alzheimer's | + | + |
| 3154 | ?/M | normal | − | − |
| 2067 | ?/M | normal | − | − |
| 3178 | ?/M | normal | − | − |
| 3227 | 22/M | normal | − | − |
| 3160 | 24/M | normal | − | − |
| 8437 | 62/M | liver cirrhosis | + | |
| 9131 | 70/M | heart failure | + | |
| 9544 | 72/M | alcoholism/infarcts | − | |
| 9945 | 86/M | pneumonia | + | |
| 8360 | 68/M | Parkinson's | + | + |
| 9821-0 | 64/M | Parkinson's | + | + |
| 9800-0 | 66/F | Parkinson's | + | + |
| 9674 | 77/M | Parkinson's | − | − |
| 7891 | 66/M | Parkinson's | − | + |
| 6166-A | 76/M | Parkinson's | − | − |
| 5407-A | 75/M | Parkinson's | − | − |
| 7749 | 75/M | Parkinson's | − | − |
| 6068 | 50/M | Parkinson's | − | − |
| 9424 | 85/M | acute hypoxia | + | + |
| 9276 | 72/F | Creutzfeldt-Jakob | + | + |
| 9124 | 76/M | Creutzfeldt-Jakob | − | |
| 9353 | 70/M | Pick's | + | + |

[a] A "+" indicates a positive response
A "−" indicates a negative response and
A blank indicates that the sample could not be analyzed.

Detection of an approximately 130 kDa polypeptide in the Alzheimer's samples required concentrating the samples to about 2.5 mg/mL and incubating the polypeptide-antibody complex once with the goat anti-rabbit IgG-alkaline phosphatase and then once with the rabbit anti-goat IgG-alkaline phosphatase. As was stated above, the amount to which the samples are concentrated depends to some extent on the sensitivity of the reporter system, the affinity of the antibodies as well as the quality of the samples. Thus, the 2.5 mg/ml figure will vary. Sensitivity of immunodetection increased about three-fold using the second incubation step. It is believed that this was due to presence of increased number of complexes as was noted above.

In 14 of 14 Alzheimer's samples, the 130 kDa polypeptide was consistently detected. The 130 kDa polypeptide was detected in only 9 of 22 non-Alzheimer's control samples.

The Alzheimer's samples and controls group did not differ significantly in their IgG or albumin content (data provided by National Neurological Research Bank) and Coomassie blue staining of SDS-polyacrylamide gels revealed no apparent differences in the level of content of any of the stained polypeptides.

These results are significant because they establish that a 130 kDa protein, in soluble form, was detected in a bodily fluid and appears to be an APP-related protein sharing at least one epitope with the C-terminus of APP corresponding substantially to amino acids 676 to 695 of APP or to a subsequence thereof.

The 130 kDa protein may be an intact APP isoform, as it co-migrates with the largest immunoreactive APP form present in rat brain. It may be an altered or homologous amyloid immunoreactive species.

In addition to the 130 kDa polypeptide, an immunopositive polypeptide of apparent molecular size of about 35 kDa was elevated in the Alzheimer's disease samples, being readily detectable in CSF of the ten Alzheimer's samples analyzed. This band was not detected in the normal controls. It was detected in 6 of 12 degenerative diseases (Parkinson's, Creutzfeldt-Jakob or Pick's), and in 1 sample having unclear neurological status (the other four samples were not analyzable).

The present results have established that a 35 kDa protein, in soluble form, was also detected in a bodily fluid and appears to share at least one epitope with the C-terminus of APP corresponding substantially to amino acids 676 to 695 of APP or to a subsequence thereof.

We claim:

1. A method to assist in the diagnosis of Alzheimer's disease comprising:
   (a) concentrating soluble proteins present in a sample of cerebrospinal fluid;
   (b) separating the concentrated proteins by sodium dodecylsulfate-polyacrylamide gel electrophoresis;
   (c) detecting the presence of proteins of apparent molecular size of about 130 kDa and about 35 kDa in the separated proteins by immunoreaction with an antibody immunoreactive with the C-terminal 20 amino acids of the human amyloid precursor protein as shown in FIG. 1.

2. A method of claim 1 wherein the proteins in the cerebrospinal fluid are concentrated in step (a) to a range from about 1.0 mg/ml to about 3.5 mg/ml.

3. A method of claim 1 wherein the proteins in the cerebrospinal fluid are concentrated in step (a) by ultrafiltration.

4. A method of claim 1 wherein the immunoreaction in step (c) is detected using an enzyme, radioisotope, chemiluminescent, fluorogenic, or electrochemical reagent.

* * * * *